United States Patent [19]

Wright et al.

[11] Patent Number: 4,702,733
[45] Date of Patent: Oct. 27, 1987

[54] FOOT ACTUATED PINCH VALVE AND HIGH VACUUM SOURCE FOR IRRIGATION/ASPIRATION HANDPIECE SYSTEM

[75] Inventors: George M. Wright, Mission Viejo; Larry W. Blake, Irvine, both of Calif.

[73] Assignee: Innovative Surgical Products, Inc., Santa Ana, Calif.

[21] Appl. No.: 801,068

[22] Filed: Nov. 22, 1985

[51] Int. Cl.⁴ .............................................. A61M 1/00
[52] U.S. Cl. ...................................... 604/34; 604/250
[58] Field of Search ..................... 604/22, 27, 28, 30, 604/33–36, 250; 128/305, 303 C, 24 A

[56] References Cited

U.S. PATENT DOCUMENTS

| | | | |
|---|---|---|---|
| 4,168,707 | 9/1979 | Douvas et al. | 128/305 |
| 4,274,411 | 6/1981 | Dotson, Jr. | 604/30 |
| 4,324,243 | 4/1982 | Helfgott et al. | 604/22 |
| 4,428,748 | 1/1984 | Peyman et al. | 128/305 |
| 4,457,747 | 7/1984 | Tu | 604/7 |

OTHER PUBLICATIONS

Site TXR Brochure, Site Microsurgical Systems, Inc., Horsham, Pa., 19044.

*Primary Examiner*—C. Fred Rosenbaum
*Assistant Examiner*—J. L. Kruter
*Attorney, Agent, or Firm*—Knobbe, Martens, Olson & Bear

[57] ABSTRACT

A pinch valve device is disclosed for a disposable, inexpensive irrigation/aspiration handpiece system used for the removal of unwanted material in a very small, enclosed operative site in which it is important to maintain pressure within a certain range, such as in the surgical operation for removal of a cataract lens from the human eye. The device includes a foot pedal for selectively: (1) restricting the flow of irrigation and aspiration fluid in the handpiece system; (2) permitting irrigation by the handpiece system, without permitting concurrent aspiration by the handpiece system; (3) permitting both irrigation and aspiration by the handpiece system; and (4) providing selective increase in aspiration force.

2 Claims, 9 Drawing Figures

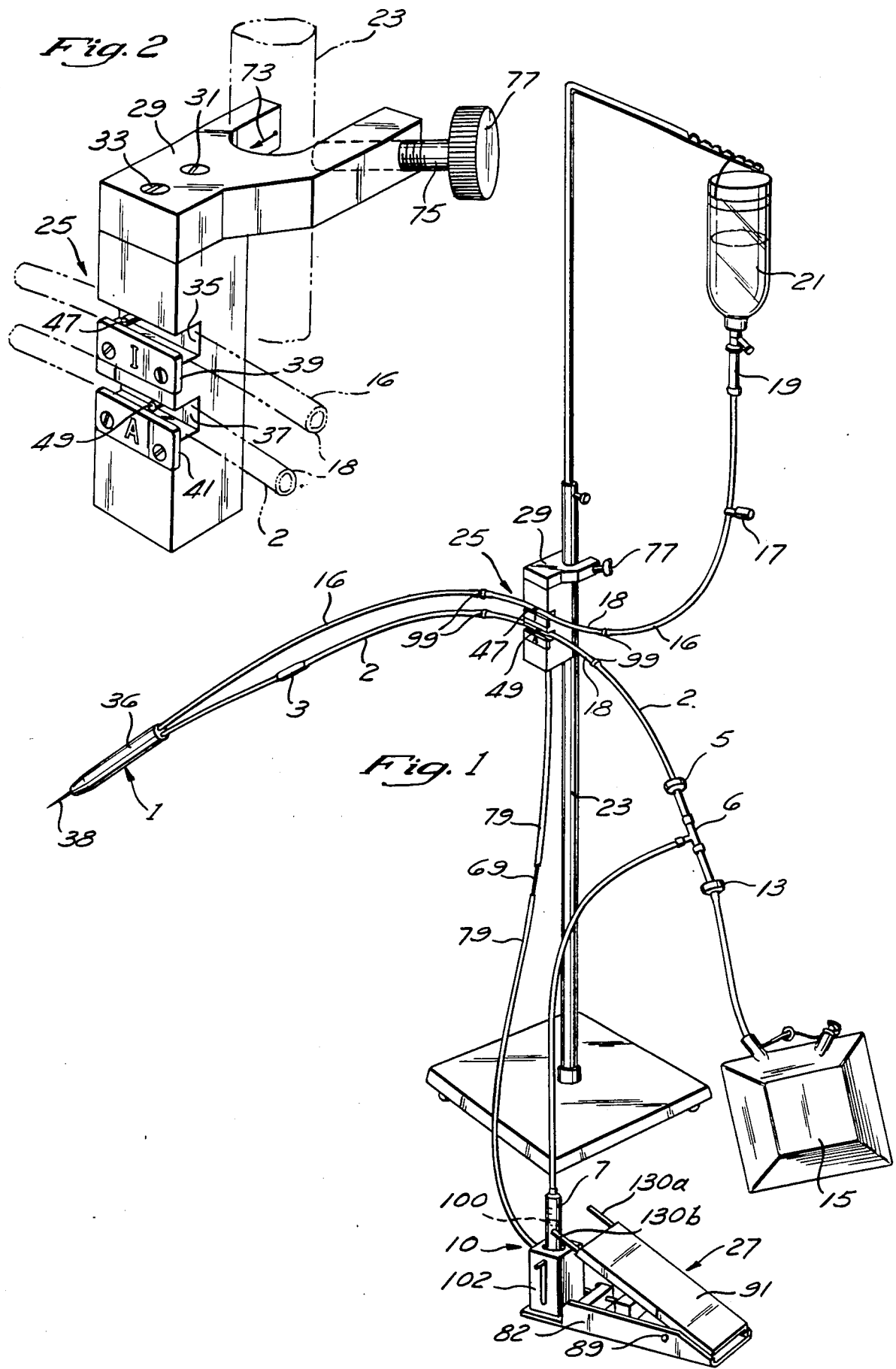

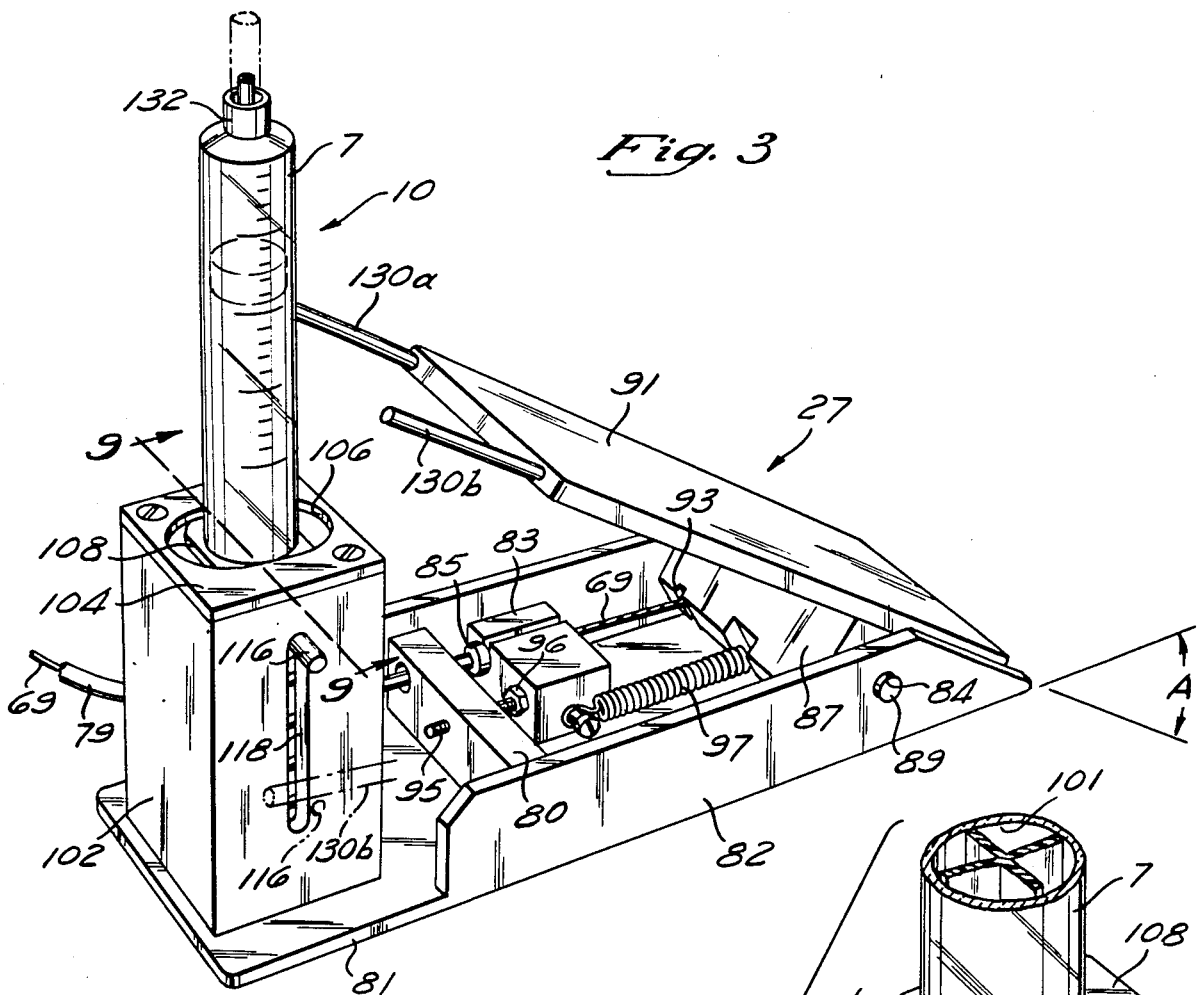
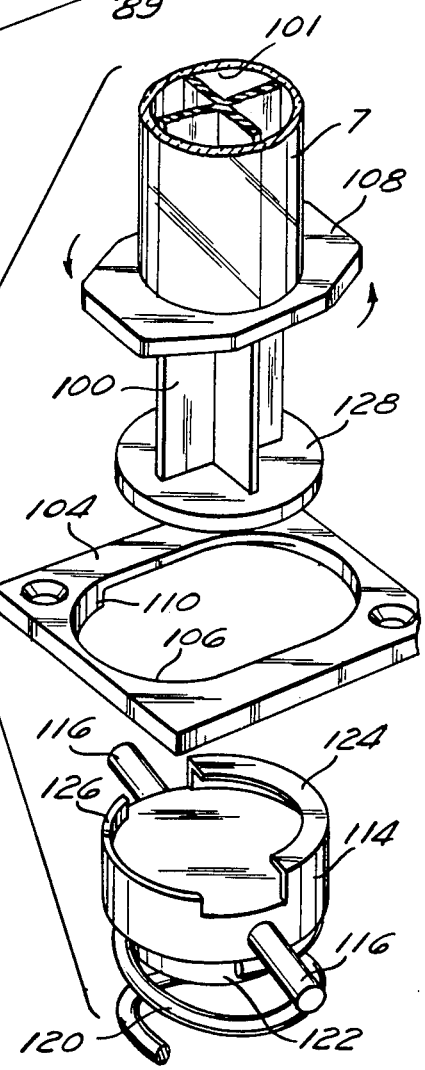
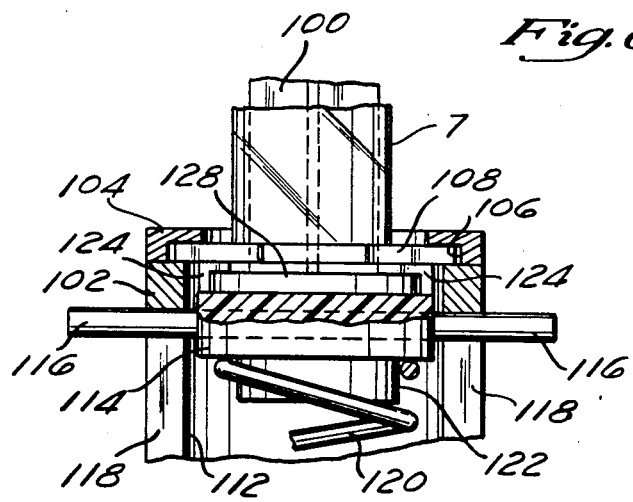

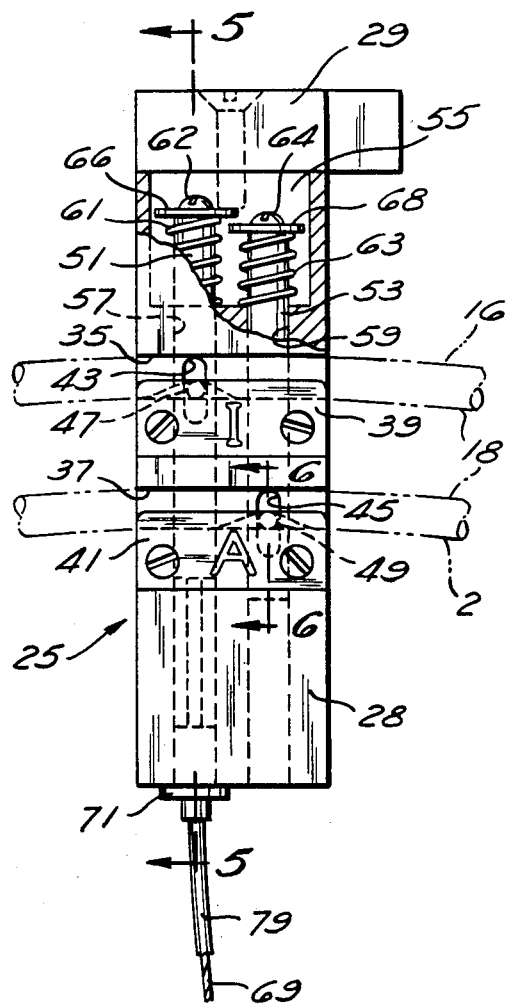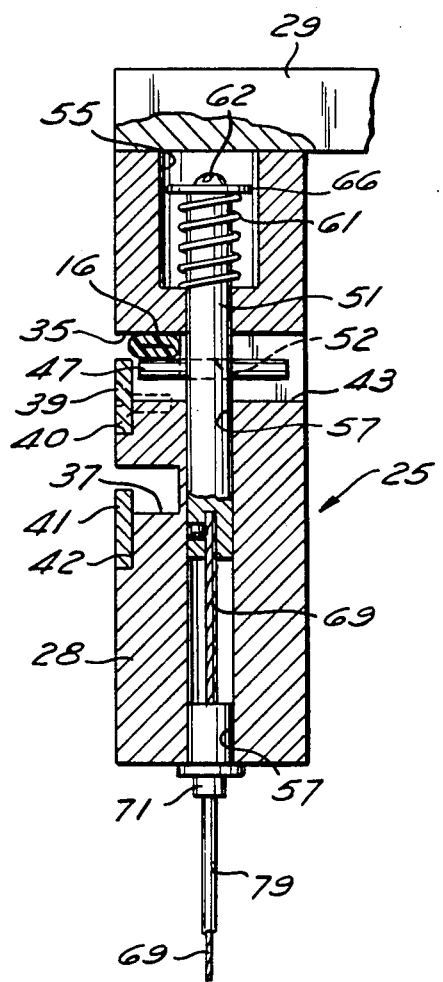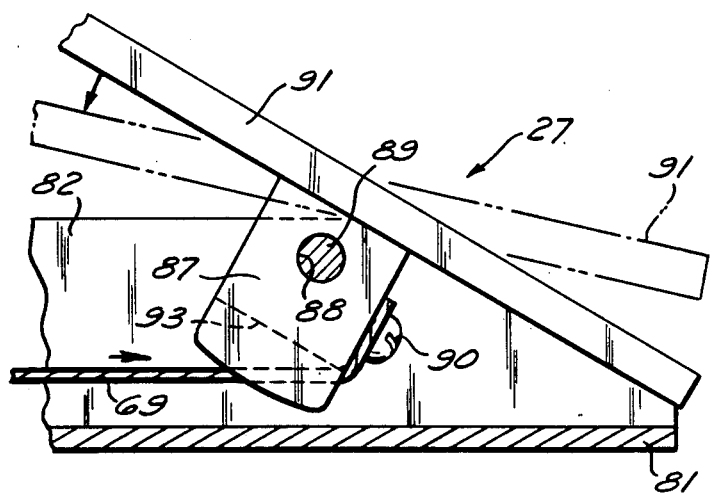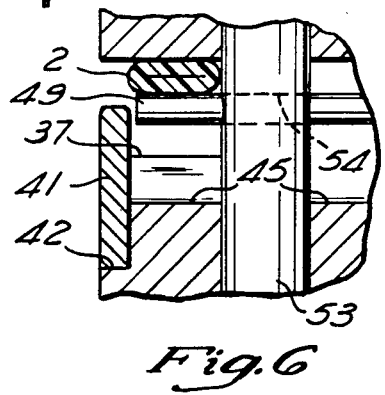
Fig. 4
Fig. 5
Fig. 6
Fig. 7

FOOT ACTUATED PINCH VALVE AND HIGH VACUUM SOURCE FOR IRRIGATION/ASPIRATION HANDPIECE SYSTEM

BACKGROUND OF THE INVENTION

The present invention relates to a flow control system to be used with a surgical handpiece, which is primarily utilized for the removal of organic tissue from an enclosed or semi-enclosed operative site. The flow system is particularly adapted for use in the removal of a cataract lens in the human eye, and thus, by way of illustration, will be described in that context.

Early techniques for cataract surgery involved intracapsular extraction, in which the lens, enclosed in its complete capsule, is entirely removed by making a 180° incision in the eye so that the cornea could be lifted and the lens removed as a whol. Current techniques involve extracapsular extraction in which the only lens contents and a portion of the lens capsule is removed. Typically the posterior capsule is left intact with the anterior capsule being partially or totally removed. Extracapsular cataract extraction is achieved by making a small incision in the eye so that the tip of a surgical handpiece can be inserted into the anterior chamber of the eye to access to the diseased lens.

Several types of handpieces currently are used in the extracapsular cataract extraction. Some handpieces use rotating or oscillating cutting devices to chop the diseased lens into small pieces while, other handpieces use phacoemulsification techniques wherein an ultrasonic needle is inserted into the lens so ultrasonic energy can affect the disintegration or emulsification of the lens. During or after disintegration of the lens, the fragments are removed from the eye.

Regardless of the technique used for fracturing and removing the lens, a cortex layer on the inner wall of the lens capsule must be removed from the operative site. This removal is typically accomplished using a handpiece which includes a tip formed as an elongate, rigid tube surrounded by a sleeve spaced from the tube, thus providing two separate flow channels. Washing fluid is introduced through the hollow sleeve at a constant pressure. This introduction of fluid, which is called "irrigation," provides a replacement for fluid and material withdrawn or lost from the eye chamber. Fluid and suspended cortex material is withdrawn from the anterior chamber through the rigid tube. This withdrawal is called "aspiration". A handpiece simultaneously irrigating and aspirating the eye is called an "IA handpiece." In practice, the tip of the IA handpiece is used to rub or abrade away the cortex layer. In some instances the irrigation and aspiration can be used to aid the cortex removal.

It is of particular importance that, during the operation, the pressure of the anterior chamber be maintained within a certain range of values, since otherwise various portions of the eye could be damaged. For example, a collapse of the anterior chamber could result in either the iris, the endothelium layer of the cornea, or the posterior capsule being damaged.

In order to insure against the collapse of the anterior chamber, complex flow control systems have been developed for supplying fluid to, and removing fluid and residue from, the handpiece flow channels. Many utilize flow transducers, a series of valves, electronic flow control devices, constant volume pumps and, of course, an electric power source for the system. These systems are quite complex and expensive. Furthermore, the complexity of these systems requires that support personnel obtain extensive training to adequately assist the doctors during eye surgery.

Other flow control systems are substantially simpler and more easily regulated by operating room personnel. They regulate the fluid flow pressure principally by adjusting the height at which an irrigation fluid source is supported above the eye. Most importantly, however, these systems use constant displacement pumps (often peristaltic pumps) to provide the suction for aspiration of the system. Periodically during the operation, the opening in the tip of the handpiece, through which the aspiration proceeds, may be occluded by large fragments of lens material or the capsule wall itself. During such occlusion, fluid is prevented from entering the aspiration channel. However, the system's constant displacement pump continues to operate, gradually constricting the resilient tubing utilized by the system until the vacuum reaches dangerous proportions. This problem is particularly acute because the total volume in the anterior chamber of the eye is very small in relation to the overall volumetric constriction of the tubing. If the resulting vacuum is now somehow released before the occlusion is dislodged from the aspiration channel, the tubing may suddenly spring back to its normal diameter, rapidly withdrawing fluid from the anterior chamber and drawing the enclosing tissues toward the handpiece tip. Either tissue contact with the aspirating channel of the handpiece, or the rapid deformation of the anterior chamber could cause irreversible injury to the patient's eye.

The flow control system for which the present pinch valve is primarily designed uses a low-cost, disposable, constant pressure vacuum source. Furthermore, the vacuum source is mechanically operated, and therefore not dependent upon an outside electrical power source; thus adding to the system's reliability.

In the event that the aspiration channel of this system is occluded, the vacuum source continues to supply only that amount of negative pressure previously supplied to the system, thus obviating the need for the vacuum release devices utilized by other irrigation/aspiration systems. However, if a greater vacuum is needed in order to clear the occlusion from the aspiration channel, this system contains a separate, low-cost, high-vacuum source which can be adjusted to provide only that vacuum necessary to dislodge the occluding matter. Although this vacuum is sufficient to clear the aspiration channel, it is not so great as to pose the danger of rapidly decompressing the anterior chamber. In the event that a safe level of vacuum is not sufficient to clear the aspiration channel, the system provides a means for the momentary reversal of the flow in the aspiration channel in order to dislodge the occlusion.

In contrast to the more complex and expensive irrigation/aspiration systems described above, a simpler irrigation/aspiration system has heretofore used a finger pinch valve to control the aspiration of the system and a separate clamp to control the irrigation of the system. This manual operation has required the surgeon to use one hand to control or adjust the system. This restriction on the use of one of the surgeons hands has limited the commercial viability of this simpler, less expensive system.

SUMMARY OF THE INVENTION

The present invention permits use of the simpler, mechanical irrigation/aspiration system while leaving the physician's hands free. This is accomplished by providing a foot-operated control of both the irrigation and aspiration of the irrigation/aspiration handpiece system. Furthermore, because physicians are familiar with more complex and expensive foot-controlled irrigation/aspiration systems, use of the present pinch valve will not require them to undergo extensive further training. Still further, the pinch valve and foot operated control are reusable in order to provide a coat effective combination of disposable parts, and reusable, durable parts.

The irrigation/aspiration system of this invention comprises an irrigation/aspiration handpiece to which one end of both an irrigation tube, and an aspiration tube are connected. The other end of the irrigation tube is connected to a fluid supply source. The other end of the aspiration tube is connected to both a constant vacuum source, and a controlled high vacuum source, such as a disposable syringe. One-way valves on the aspiration tubing prevent unintended changes in pressure at the handpiece. Both the irrigation and aspiration tubes are connected to pinch valves which can restrict the tubing to regulate the fluid flow within the tube. A foot pedal controls the actuation of the pinch valve, and also controls the operation of the high vacuum means such as the disposable syringe.

The foot control of the present invention rests upon the floor during the operation. When the foot control is released, pinch valves completely restrict the irrigation and aspiration of the handpiece system. When the physician desires to irrigate the operative site without its concurrent aspiration, the physician partially depresses the foot pedal. This causes the pinch valve to unclamp the irrigation tubing of the system, thus allowing irrigation to occur. When the physician requires both irrigation and aspiration by the handpiece system, he depresses the foot pedal further, thus unclamping the aspiration tubing and providing for the concurrent irrigation and aspiration of the operative site. If the physician requires still more auction or aspiration, he depresses the foot pedal still further to engage a vacuum drawing syringe, connected to the aspiration line.

The pinch valve device is compact, thereby permitting easy shipping and storage of the device. It is relatively easy to manufacture, thereby providing lower cost. It is simple and reliable. The syringe provides a controlled, but high vacuum reservoir that is also simple, reliable, low cost, and disposable. The foot pedal control provides a compact device which leaves the physicians hands free.

BRIEF DESCRIPTION OF THE DRAWING

FIG. 1 is a perspective view of the irrigation/aspiration handpiece system in its assembled condition;

FIG. 2 is a perspective view of the pinch clamp of the irrigation/aspiration handpiece system;

FIG. 3 is a perspective view of a foot pedal and high vacuum means of the irrigation/aspiration handpiece system;

FIG. 4 is a front elevation view, partially in section, of the pinch clamp;

FIG. 5 is a sectional view of the pinch clamp taken along line 5—5 of FIG. 4;

FIG. 6 is an enlarged portion of the sectional view taken along line 6—6 of FIG. 4, showing operation of the pinch clamp;

FIG. 7 is a sectional view showing the fulcrum assembly of the foot pedal;

FIG. 8 is an exploded perspective view showing the connection of a syringe to the foot pedal of FIG. 3; and FIG. 9 is a sectional view taken from 9—9 of FIG. 3 showing the connection of the syringe with the foot pedal.

DESCRIPTION OF THE PREFERRED EMBODIMENT

During a typical cataract removal operation, the physician first makes an incision in the eye to provide access to the anterior chamber. Then a systatome handpiece is used to cut through the anterior capsular bag. The physician the inserts the lip of a surgical handpiece into the anterior chamber and affects the disintegration of the diseased lens, as for example, by ultrasonic emulsification. During this disintegration process, the lens fragments are removed from the eye chamber. By aspiration through the phaco needle.

After the lens is removed, the cortex is removed by the irrigation/aspiration handpiece system. The cortex is a layer of cells inside the lens capsule. If not removed, this layer will contact the replacement lens and opacify (turn white) with time, thus inhibiting clear vision. Removal of the layer inhibits opacification by preventing or inhibiting the regeneration of the cortex.

Referring initially to FIG. 1, the irrigation/aspiration handpiece system is shown perspectively in its assembled condition. In a brief overview of the system's operation, the physician clasps an irrigation/aspiration handpiece 1 in one hand, while controlling the irrigation and aspiration of the handpiece 1 by use of a foot pedal assembly 27. Until pressure is applied to the pedal 91 foot pedal assembly 27, pinch clamps 25 tightly pinch a pair of tubes 2 and 16 through which the aspiration and irrigation fluids flow, respectively, thereby preventing aspiration or irrigation by the handpiece 1. The physician inserts the tip 38 of the irrigation/aspiration handpiece 1 into the anterior chamber of the eye and begins irrigation at the handpiece 1 by partially depressing the pedal 91, causing the clamp 25 to unpinch the irrigation tube 16 connected to a pressurized source of fluid, such as an I.V. bottle 21 which communicates with the handpiece 1, and allows flow of irrigation or washing fluid to the eye chamber. The physician begins aspiration by further depressing the pedal 91, causing the clamp 25 to unpinch the aspiration tube 2 connecting the irrigation/aspiration handpiece 1 to a vacuum reservoir 15.

Should the aspiration inlet of the handpiece 1 occlude, the physician can depress the pedal 91 still further until an increased suction source 10, such as syringe 7, activates to provide an increased vacuum to clear the handpiece 1. A one-way valve 13 prevents the vacuum supplied by high vacuum source 10, such as a syringe 7 and piston 100, from withdrawing fluid from a constant vacuum reservoir 15. Thus, when the syringe 7 is used, its vacuum communicates only with the handpiece 1.

If the application of a safe level of vacuum is insufficient to clear the aspiration channel 2 the physician, with his free hand, may pinch a reflux bulb 3, momentarily pressurizing the aspiration channel 2 and reversing the flow in the aspiration channel 2 of the handpiece 1 to dislodge the occluding matter. A one-way valve 5 permits the syringe 7 to be flushed without contaminating the aspiration channel 2, and handpiece 1, with previosly-withdrawn fluid. This flushing of the syringe 7 permit multiple strokes of the piston 100 of syringe 7 for extended high-vacuum operation. The system thus allows the physician, without the aid of an attendant, to selectively control both the irrigation and aspiration of the eye chamber during the cataract removal operation.

In greater detail, a pressurized source of fluid is provided by a standard I.V. bottle 21, containing washing fluid, which is suspended from an I.V. pole 23 at a height calculated to create the proper fluid pressure in the irrigation channel 16 and the irrigation/aspiration handpiece 1. A drip chamber 19 is inserted into the I.V. bottle 21 in the customary manner, providing a visual indication of the flow of washing fluid to the handpiece 1. One end of irrigation tube 16 is fitted tightly over the male fitting of the drop chamber 19, creating a tight seal; the opposite end is similarly attached to the irrigation inlet of the irrigation/aspiration handpiece 1. Thus, the irrigation tube 16 communicates with the pressurized fluid source of elevated bottle 21, and the irrigation/aspiration handpiece 1.

As a further means of controlling the flow rate between the I.V. bottle 21 and the irrigation/aspiration handpiece 1, a plastic clamp 17 is attached to the exterior of the irrigation tube 16 proximate to the drip chamber 19. This plastic clamp 17 contains a screw mechanism for manually constricting the diameter of the irrigation tube 16 so that the flow rate within the tube 16 can be set at a predetermined rate.

Between the handpiece 1 and the clamp 17 the irrigation tube 16 passes through the pinch clamp 25. The tube 16 is typically made of PVC plastic, but has a more flexible segment, typically made of silicone rubber, with the silicone rubber segment passing through the pinch valve 25. The PVC can be joined to the silicone rubber 18 by forcing the silicone tube over the PVC tube, or by the use of Laur-Lock fittings which are known in the art and not described in detail herein.

As seen in FIG. 2, the irrigation tube 16 running from the drip chamber 19 to the irrigation channel of the irrigation/aspiration handpiece 1 is maintained in an upper channel 35 of the pinch clamp 25 by the three walls of the channel, and a channel cover plate 39. The channel cover plate 39 partially blocks the channel face, permitting the irrigation tube 16 to be forced into the channel 35 during assembly of the system, but serving to contain or secure the tube 16 within the channel 35 during operation.

The irrigation tube 16 is positioned above an irrigation channel clamp pin 47 within the channel 35. The channel clamp pin 47 reciprocates vertically, as viewed in FIG. 2. At one extreme of the reciprocation, the pin 47 pinches the irrigation tube 16 between itself and the upper wall of the irrigation channel 35, thereby restricting the flow of washing fluid in the tube 16. At the other extreme of its reciprocation, the pin 47 loosely contacts the tube 16, permitting fluid to flow from the I.V. bottle 21 to the irrigation/aspiration handpiece 1. The structural features of the pinch valve 25 will be discussed in greater detail after the other system components have been described.

Referring again to FIG. 1, the irrigation/aspiration handpiece 1 has an elongate cylindrical body 36 of unbreakable material which tapers and is grooved in order to facilitate non-slip gripping. The handpiece 1 has two separate channels: an aspiration channel connected to a rigid, elongate, hollow metal needle having a small hole which provides the aspiration channel inlet; and an irrigation subsystem, typically coaxial with the aspiration channel. Both the irrigation and aspiration channels communicate with the body cavity through the handpiece tip 38.

The aspiration channel of handpiece 1 is connected to a reflux bulb 3 by the aspiration tube 2. Preferably made of clear plastic, the reflux bulb 3 generally permits the unrestricted flow of waste fluid and residue between the handpiece 1 and the constant pressure vacuum reservoir 15 excerting a constant negative pressure. However, when depressed, the bulb 3 restricts the aspiration channel at the end of the bulb distal the handpiece 1 and forces the fluid contained in the bulb 3 back through the aspiration channel, thus forcing fluid out of the handpiece tip 38 and serving to dislodge any occlusion present at the inlet of the aspiration channel.

Referring to FIGS. 1 and 2, the aspiration tube 2 also passes through the pinch clamp 25. The aspiration tube 2 is typically made of PVC, while the segment of the aspiration tube 2 passing through the pinch valve 25 is made of more flexible material such as silicone rubber. The connection between the PVC and silicone rubber is made as previously described with respect to the irrigation tube 16.

The aspiration tube 2 connects the reflux bulb 3 to a high vacuum source 10 and to the constant pressure vacuum reservoir 15. The aspiration tube 2 is maintained in a lower channel 37 of the pinch clamp 25 by the three walls of the channel 37 and a channel cover plate 41. The channel cover plate 41 partially blocks the channel 37 face, permitting the flexible aspiration tube 2 to be squeezed or forced into the channel 37 during assembly of the system, but serving to secure the tube 2 within the channel 37 during operation.

The aspiration tube 2 is positioned above an aspiration channel pin 49 within the channel 37. The channel pin 49 reciprocates vertically, as viewed in FIG. 2. At one extreme of the reciprocation, the pin 49 pinches the aspiration tube 2 against the upper wall of the aspiration channel 37, thereby restricting the flow of washing fluid sucked through the aspiration tube 2. At the other extreme of its reciprocation, the pin 49 loosely contacts the aspiration tube 2, permitting fluid to flow from the irrigation/aspiration handpiece 1 to the low vacuum reservoir 15 or the high vacuum means 10.

Referring once again to FIG. 1, in order to avoid fluid flow back toward the handpiece 1 from the high vacuum source 10 or from the low vacuum reservoir 15 to the high vacuum source 10, two one-way valves 5,13 are connected to the aspiration tube 2 on opposite sides of the connector 6. The connector 6 can take the form of a Y or T connector. Thus, one-way valve 5 is on the upstream side of connector 6, toward handpiece 1. One-way valve 13 is between the connector 6 and the low vacuum reservoir 15. These one-way valves allow the vacuum created by the high vacuum source 10, such as the syringe 7, to be communicated to the aspirating tip 38 of the handpiece 1, but not to the low-vacuum reservoir 15. The valves 5,13 further permit the positive pressure, created when the syringe 7 is flushed, to be communicated to the low vacuum reservoir 15, but not the aspiration channel of the handpiece 1.

The low vacuum reservoir 15 is preferably a flexible, compressible 400 ml. reservoir which draws a substantially constant vacuum, as described in U.S. Pat. No. 4,429,693 to Blake, et al. Briefly, the reservoir utilizes a compression spring between two winged plates to expand the reservoir and create a vacuum therein. Because of the unique geometry of the plates, the spring works on a steadily decreasing effective area, thus providing the nearly constant vacuum.

Referring now to FIGS. 2, and 4-6, the pinch clamp 25 has a largely rectangular body 28 which is connected to a generally U-shaped upper yoke 29 by plural screws 31,33. The body 28 of the pinch valve 25 has two horizontal rectangular channels 35,37 into which the silicon irrigation and aspiration tubes 16,2, respectively, are fitted during operation of the system. Coincident with the lower edge of each channel 35 and 37, is a horizontal rectangular recess 40,42 respectively (FIG. 5) into which the rectangular cover plates 39,41 respectively are fitted and attached to the body with screws. These plates 39,41 partially block the channels 35,37, respectively, and, as previously described, serve to aid in holding the irrigation and aspiration tubes 16,2 respectively, securely in place during operation.

To guard against the improper assembly of the irrigation/aspiration system, the upper plate 39 is inscribed with the letter "I", for irrigation, and the lower plate 41 is inscribed "A", for aspiration (FIGS. 2 and 4).

Referring to FIGS. 4 and 5, the body 28 of the pinch clamp 25 contains a box-shaped cavity 55 on the end of the body 28 adjacent to the yoke 29. Two proximally located vertical bores 57,59 connect the cavity 55 to the opposing end of the clamp body 28. As viewed in FIG. 4, an aperture 43 connects the left bore 57 to the irrigation channel 35, and a second aperture 45 connects the right bore 59 to the aspiration channel 37. Within each of the bores 57,59 is an elongate, rigid cylindrical shaft 51,53 respectively, of a diameter sufficiently smaller than that of its bore 5/,59 as to permit vertical reciprocation of the shafts 51,53 within the bores 57,59. Each shaft 51,53 has an aperture 52,54 respectively, (FIGS. 5 and 6). Channel pins 47 and 49 are inserted into, and extend radially from, the apertures 52 and 54, respectively, so as to be held firmly by the shafts 51 and 53, respectively. The extending portion of channel pins 47 and 49 extend through apertures 43 and 45, respectively, and into channels 35 and 37 respectively. The apertures 52,54 are so located on the shafts 51,53, respectively that when both pins 47,49 are flush against the upper wall of their respective channels 35,37, the top of the right shaft 53 (FIG. 4) is nearer the base of the cavity 55 than the top of the left shaft 51.

As shown in FIG. 4, about each shaft 51,53 is an axially precompressed compression spring 61,63 respectively, which presses against the bottom of a washer 66,68, respectively, secured to the shaft 51,53, respectively, by a screw 62,64, respectively, thereby biasing the shaft 51,53 upward so that its respective pin 47,49 tightly presses against the upper wall of its channel 35,37. The washers 66,68 are chosen so that when the left shaft 51 (as viewed in FIG. 4) reciporocates downward within its bore 57, its washer 66 will securely engage the washer 68 of the right shaft 53, thereby forcing the right shaft 53 and its associated pin 49 to reciprocate downward. In short, the washers 66,68 overlap so the shafts 51,53, and hence the pins 47 and 49, are reasonably coupled after the washers 66,68 contact.

Attached to the lower end of the left shaft 51 (FIG. 4) is a flexible metal cable 69. When the tension on the cable 69 is less than the biasing force of the left shaft's compression spring 61, the pins 47, 49 firmly pinch the tubes 16,2 against the upper walls of their respective channels 35,37, thus completely restricting the flow of fluid in the tubes 16,2.

Referring to FIGS. 1, 4, and 5, as the tension on the cable 69 increases sufficiently to overcome the biasing force of the left shaft's compression spring 61, the left shaft 51 moves downward within its vertical bore 57, thereby lowering the pin 47 in the irrigation channel 35 and permitting the free flow of washing fluid from the I.V. bottle 21 (FIG. 1) to the handpiece 1. As the tension is further increased, the washer 66 of left shaft 51 (FIG. 4) comes into contact with the washer 68 of the right shaft 53. At this point, there is a range of increased tension in cable 69 which will be accompanied by no shaft movement, as now the biasing force of both of the springs 61,63 needs to be overcome. If tension in cable 69 is increased sufficiently to overcome the combined force of the springs 61,63, the shafts 51,53 will move downward within their bores 57,59, lowering the pin 49 in the aspiration channel 37 and permitting the free flow of waste fluid and residue from the handpiece 1 to the constant vacuum reservoir 15.

The resistance of the spring 61 alone, and springs 61,63 combined, perceptibly increase the tension which must be applied to cable 69 in order to unclamp the tubes 2,16 to increase the irrigation and aspiration, respectively. This perceptible change in resistance, or tension, of the cable 69, can be used by the operator of the handpiece 1 to selectively control the irrigation and aspiration of the operative site.

Referring to FIGS. 4 and 5, at the base of the left shaft bore 57 is a plug 71 which abuts against the bottom of body 28 of pinch clamp 25 plug 71 is the termination point of a wound wire sheath 79 which surrounds the cable 69 and permits low friction movement of the cable 69 relative to the sheath 79.

Referring now to FIGS. 2 and 4, the upper yoke 29 is a generally U-shaped plate with two vertical countersunk bores. Two screws 31,33 (FIG. 2) attach the body 28 to the yoke 29. The inner radius 73 (FIG. 2) of the yoke 29 of the pinch clamp 25 is sized to provide a close fit of the yoke 29 about a standard I.V. pole 23 (FIGS. 1 and 2). One arm of the yoke 29 contains a threaded bore. A threaded bolt 75 with a disc-shaped, serrated, hard plastic handle 77 is threadably inserted through the threaded bore and tightened sufficiently to securely anchor the pinch clamp 25 to the I.V. pole 23.

As seen in FIG. 1, the sheathed cable 69.71 has one end connected to the pinch clamp 25 and the other end connected to the foot pedal assembly 27. Referring to FIGS. 1, 3 and 7, the foot pedal assembly 27 has a pedal 91 which is a generally rectangular metal plate with beveled edges. Attached to the bottom of this foot pedal 91, and at one end thereof, is a fulcrum block 87. The fulcrum block 87 is a rectangular block with rounded edges and a bore 88 approximately three-fourths of the way from its base along its center line.

The foot pedal assembly 27 also has a base 81 (FIG. 3) which is a generally rectangular plate with perpendicularly aligned flanges 82 along its length. At one end of the base 81, these flanges are cut to form approximately a 30-degree angle A, with the base 81 (FIG. 3). Each flange 82 has an aperture 84 proximate the angled portion of the flange 82 which, when aligned with the bore 88 of the fulcrum block 87, provides the orifice through which is fitted a fulcrum pin 89, about which the pedal 91 rotates (FIG. 7).

The metal cable 69 connects the base of the left shaft 51 (FIG. 4) to the pedal 91. As can be seen from FIG. 3, the sheath 79 surrounding the cable 69 passes through a bore in a protective block 80 connected to the foot pedal base 81, and terminates at a plug 85. The plug 85 is secured to an adjustment block 83 which has a bore through which the unsheathed cable 69 extends to a channel 93 at the base of the fulcrum block 87. The cable 69 extends beyond the length of the channel 93 and is securely attached to the side of fulcrum block distal the adjustment block 83 by a screw 90 (FIG. 7). Thus the rotation of the pedal 91 about fulcrum pin 89 causes the fulcrum block 87 to pull the cable 69 while the sheath 71 is restrained by the plug 85. Thus the foot pedal assembly 27 can apply tension to the cable 69 and the pinch valve 25.

Referring to FIG. 3, the adjustment block 83 allow adjustment of the initial tension of the cable 69. A bore through the protective block 80 allows a threaded fastener, such as a bolt 95, to be inserted through the fastener, such as bolt 95, to be inserted through the protective block 80, substantially parallel to the base 81. The bolt 95 extends into a correspondingly located threaded aperture in the positioning block 83. A nut 96 is threaded onto the bolt 95 intermediate the protective block 80 and the positioning block 83. The bolt 95 allows adjustment of the distance between between the protective block 80 and the adjustment block 83, and hence allows adjustment of tension of cable 69. After the position of the adjustment block 83 is adjusted to provide the correct tension in cable 69, then the nut 96 is screwed against the side of the adjustment block 83 in order to prevent unscrewing of the bolt 95 and hence a change in the tension of cable 69.

Once positioned, the adjustment block 83 is then secured to the flange 82 by means well-known in the art and not illustrated in detail herein. Briefly, a screw can extend through a slotted aperture in flange 82, in order to allow positioning of the adjustment block 83 along the length of the flange 82 as the screws slides the slot. The screw can then be tightened in order to releaseably fix the position of the adjustment block 83.

A tension spring 97 is connected between the adjustment block 83 and the fulcrum block 87. The tension spring 97 causes the pedal 91 to rotate about the fulcrum pin 89 until one end of the pedal 91 contacts the base 81. Thus, the tension spring 97 preloads the pedal 91 into a predetermined position and provides a resistance to rotation of the pedal 91 about fulcrum pin 89.

Referring now to FIGS. 1, 3, 8 and 9, the operation of the high vacuum source 10 will be explained. Briefly, a syringe, 7 is connected to the aspiration tube 2, and also connected to the foot pedal 27 so that it can be controllably activated by depression of the pedal 91, which pedal 91 also controls the irrigation and aspiration of the irrigation/aspiration handpiece 1.

Referring to FIGS. 3 and 8, a syringe 7 has a generally cylindrical cavity into which piston 100 is fitted so that a vacuum is created as piston 100 is withdrawn from the cavity 101, and pressure is increased as piston 100 is inserted into the cavity 101. The piston 100 can reciprocate in the cavity 101 to alternately create a negative (vacuum) or positive pressure. The syringe 7 and piston 100 are inserted into a housing 102 (FIG. 3) such that the syringe 7 is held stationary while the piston 100 can be withdrawn to create a vacuum in the syringe 7.

Referring to FIG. 3, the housing 102 is a tubular, rectangular structure having one end attached to the end of the base 81 opposite the fulcrum pin 89. The end of the tubular housing 102 opposite the base 81 is covered by a retainer cap 104. The retainer cap 104 is shown fastened to the housing 102 by the use of threaded fasteners, such as screws.

Referring to FIGS. 3 and 8, the retainer cap 104 has a centrally located, oblong aperture having a major axis along the longer portion of the aperture 106, and a minor axis along the shorter width of the aperture 106. The size and shape of the oblong aperture 106 correspond to, but are slightly larger than, the size and shape of an oblong flange 108 (FIG. 8) located on one end of the syringe 7. The oblong flange 108 also has a major axis located along the length of the flange 108, and a minor axis located along the width of the flange 108.

When the major and minor axes of the oblong flange 108, are aligned with the major and minor axes of the oblong aperture 106 (FIG. 8), the flange 108 can be inserted through the aperture 106. If the flange 108 is rotated one quarter turn, or approximately 90°, the flange 108 cannot be withdrawn through the aperture 106 (FIG. 3).

As shown in FIG. 8, the retainer cap 104 is not of a constant thickness. Thus the flange 108 can be rotated one quarter turn, before contacting an increase in the thickness of the retaining cap 104 such as ridge 110. The bottom of ridge 110 abuts against the top of the tubular housing 102. Thus, when the flange 108 is inserted through aperture 106 and rotated one quarter turn, the flange 108 abuts against the ridge 110 and is prevented from further rotation.

Referring to FIG. 9, the housing 102 has a central aperture 112 (FIG. 9) which is generally cylindrical in shape. The diameter of the aperture 112 is less than the length of the oblong flange 108 along the major axis. The housing 102 prevents the flange 108 and thus the syringe 7, from being inserted substantially below the retainer cap 104. Thus, the retainer cap 104 retains, or lock the syringe 7 into position in the housing 102, with the ridge 110 blocking further rotation, and the retainer cap 104 and the housing 102 preventing removal along the length of syringe 7.

Referring to FIGS. 8 and 9, placed within the central aperture 112 of the housing 102 is an axially reciprocating lock piece 114. The lock piece 114 conforms to the shape of the central aperture 112, but is slightly smaller in diameter so as to be moveable along the longitudinal axis of the central aperture 112. Thus, the lock piece 114 is shown as having a circular shape (FIG. 8), and is preferably made out of a hard, tough plastic.

A metal pin 116 is inserted radially through the lock piece 114 such that the pin 116 extends beyond the lock piece 114. Referring to FIGS. 3 and 9, there are slots 118 in opposing sides of the housing 102, the slots 118 running along the length of the central aperture 112. The pin 116 extends through the slots 118 and protrudes beyond the housing 102.

Referring to FIGS. 8 and 9, the lock piece 114 is preloaded against the retainer cap 104 by a compression spring 120. The compression spring 120 surrounds, and is centrally positioned by, a cylindrical protrusion 122 on the bottom of the lock piece 114, which is opposite the retainer cap 104. The compression spring 120 is compressed between the base 81 and the lock piece 114 and retainer cap 104 so as to continually urge the lock piece 114 against the retainer cap 104.

Referring to FIG. 8, the end of the lock piece 114 adjacent the retainer cap 104 has a retaining flange 124 along one portion of the circumference of the lock piece 114. The retaining flange 124 has a generally "L" shape cross section and extends approximately 3/32 of an inch axially above the end of the lock piece 114, and extends radially inward approximately 3/16 from the edge of the lock piece 114. The flange 124 extends along an arc of approximately 120° around the circumference of lockpiece 114.

Opposite the flange 124 is a retainer wall 126 which comprises a thin axial projection extending approximately 3/32 of an inch above the top of the lock piece 114. The retainer wall 126 extends along the circumference of the lock piece 114 for approximately 120°.

As shown in FIG. 8, and especially FIG. 9, the flange 124 and retainer wall 126 cooperate with a circular flange 128 on the end of piston 100 so as to allow the flange 128 to be inserted through the aperture 106 and beneath the flange 124 and against the retainer wall 126, so as to releaseably retain the flange 128. Thus, the size and shape of flange 128 and retainer wall 126, cooperate with the size and shape of flange 128 on piston 100, in order to releaseably retain the flange 128.

In short then, the flange 128 of piston 100 is inserted into, and releaseably retained by, the lock piece 114. The flange 108 on syringe 7 is inserted into, and releasably retained by, retainer cap 104. However, the lock piece 114, and hence the flange 128 and piston 100, can be axially moved by overcoming the force of compression spring 120.

Referring to FIGS. 1 and 3, two rods, 130a and 130b, are inserted into the ends of the pedal 91 opposite the end connected to fulcrum pin 89. The rods 130 extend parallel to the length of the pedal 91 and are adjacent the edges of the pedal 91. The spacing of the rods 130 is sufficient to prevent hitting the housing 102, but close enough together to engage opposite ends of pin 116, which in turn is connected to the lock piece 114.

Thus, depression of the pedal 91 causes the rods 130 to engage the pin 116 and thus to move the pin 116, the lock piece 114, and the piston 100, axially downward against the force of compression spring 120. Moving the piston 100 downward along the length of the central aperture 112 creates a suction in the syringe 7. The end of the syringe 7 has a threadable connection 132 (FIG. 3) which is connected to the aspiration tube 2. Thus, depression of the pedal 91 exerts a controllable increase in the vacuum in the aspiration tube 2.

Foot pedal assembly 27 controls irrigation, aspiration, and increased aspiration as needed. Referring to FIGS. 1 and 4, when no pressure is applied to the pedal 91, the channel pins 47,49 tightly pinch the tubes 16,2 against the top of their respective channels 35,37 (FIGS. 5 and 6). As sufficient pressure is applied to overcome the preload of the spring 61 about the left shaft 51 (FIG. 4), the pin 47 in the irrigation channel unclamps the irrigation line 16, thereby permitting the free flow of the fluid through the tube 16. As the pressure applied to the foot pedal 91 increases, the washer 66 secured to the left shaft 51 engages the washer 68 secured to the right shaft 53. At this point, the foot pedal 91 resistance increases perceptibly, as, for further movement, the biasing force of two compression springs 61,63 needs to be overcome. When the pressure on the foot pedal 91 is sufficiently increased, the washer 66 secured to the left shaft 51 forces the right shaft 53 down in its vertical bore 59, permitting the free flow of fluid in the silicon tube 2.

Whenever the pressure on the foot pedal 91 is sufficiently decreased, the compression springs 61,63 will force the shafts 51,53 upward in their vertical bores. This will cause the aspiration channel pin 49 to pinch the aspiration tube 2, restricting the flow of fluid to the constant vacuum reservoir 15 and the high vacuum source 10. If the pressure on the foot pedal 91 is further decreased, the washer 66 secured to the left shaft 51 will disengage from the washer 68 secured to the right shaft, so that only the compression spring 61 of the left shaft, 51 is forcing the left shaft 51 upward within its vertical bore 57. Finally, when the pressure on the foot pedal 91 is less than the biasing force of the left shaft's compression spring 61, the left shaft's compression spring 61 will cause the irrigation channel pin 47 to pinch the irrigation tube 16, thus restricting the flow of fluid to the handpiece 1.

If the foot pedal 91 is depressed sufficiently to engage the pins 116, then there is a further perceptible resistance in movement of pedal 91 as the resistance of compression spring 120 must also be overcome. Further depression of pedal 91 controllably engages the vacuum in the aspiration tube 2. The rapidity with which the pedal 91 is depressed affects the rapidity with which the vacuum of syringe 7 is applied, thus providing further flexibility to the uses of the system. As the pressure on pedal 91 decreases, compression spring 120, and spring 97, urge the pedal 91 to its original position. Compression spring 120 also urges piston 100 into syringe 7 and expels any fluid into the aspiration tube 2. The one way valve 5 prevents this expelled fluid, and the resulting pressure increase, from affecting the handpiece 1.

Thus, a foot pedal can be used to control the irrigation and aspiration during surgery, and to intermittently introduce an additional vacuum source as needed. The use of spring biasing, which must be overcome in order to increase the irrigation, aspiration and additional vacuum, provides a perceptible means by which a physician can control the amount of irrigation, aspiration, and high vacuum, while having both hands free for surgery.

In a typical eye operation, the irrigation/aspiration handpiece system is assembled before the cataract lens removal operation. After making a small incision in the eye, the physician inserts the tip of the irrigation/aspiration handpiece 1 into the anterior chamber of the eye and partially depresses the pedal 91, beginning irrigation by the system and maintain a proper pressure level in the anterior chamber. When the handpiece 1 is properly oriented, the physician further depresses the pedal 91, thus beginning aspiration of the waste materials from the anterior chamber while maintaining proper anterior chamber pressure through concurrent irrigation. Should a high vacuum be desired, as by occlusion of the handpiece tip 38, the physician can further depress the pedal 91 to apply an increased vacuum by means of the syringe 7, or depress the reflux bulb 3 in an effort to remove the occlusion.

From time to time during the operation, the physician may lessen the amount of pressure on the pedal 91, thus closing the aspiration 2 but not the irrigation tube 16, and reorient the handpiece 1 in order to begin further aspiration.

Upon completion of the operation, pressure is withdrawn from the pedal 91, terminating irrigation and aspiration by the system, and the handpiece tip 38 is removed from the anterior chamber. The pedal 91 is then depressed so that the tubing 16, 2 can be removed from the pinch clamp channels 35, 37. The entire system, save for the pinch clamp 25, foot pedal assembly 27, connecting cable 69, sheath 71 and the I.V. pole 23, are then disposed of. The non-disposable elements are thus immediately available, as they need not be sanitized, for another cataract removal operation.

In another variation of this invention, the connector 6 can be directly connected or fastened to the end of the syringe 7, so as to eliminate the length of tubing between the connector 6 and syringe 7.

In yet another variation of this invention, the connection between the flexible silicone portion of the tubes 2 and 16 which passes through the pinch valve 25, and the less flexible PVC tubing connected to the handpiece 1, is made through reusable connectors 99. The connectors 99 are thus intermediate the pinch valve 25 and the handpiece 1, and can be the Laur-Lock fitting which was previously mentioned. The connectors 99 allow the handpiece 1 to be disconnected, disposed of, and replaced with a new handpiece 1, without replacing the rest of the system. Thus a separate handpiece1 can be used with each new patient, while the rest of the disposable system can be replaced only at the end of the day.

We claim:

1. An irrigation/aspiration handpiece system comprising:
   a pressurized source of fluid;
   a source of constant vacuum;
   a handpiece with a first channel connected by a first flexible tube to said fluid source and a second channel connected by a second flexible tube to said source of constant vacuum;
   a pinch clamp into which said first and second tubes are inserted, adapted to control the flow of fluid in said system by the selective compression and release of said tubes;
   a foot pedal mechanically connected to said pinch clamp to control said compression and release of said tubes by said pinch clamp, said pinch clamp comprising a first and second shaft adapted to reciprocate within said pinch clamp in response to said mechanical connection, said first shaft connected to reciprocate in direct response to movements of said foot pedal, said second shaft connected to reciprocate in response to reciprocation of said first shaft; and
   a high vacuum source controlled by said foot pedal and communicating with said second channel to provide a controlled source of increased vacuum to said handpiece.

2. An irrigation/aspiration hand piece system comprising:
   a pressurized source of fluid;
   a source of constant vacuum;
   a hand piece with a first channel connected by a first flexible tube to said fluid source and a second channel connected by a second flexible tube to said source of constant vacuum;
   a pinch clamp into which said first and second tubes are inserted, adapted to control the flow of fluid in said system by the selective compression and release of said tubes;
   a foot pedal mechanically connected to said pinch clamp to control said compression and release of said tubes by said pinch clamp; and
   a first and second shaft adapted to reciprocate within said pinch clamp in response to said mechanical connection, said first shaft connected to reciprocate in direct response to movements of said foot pedal, said second shaft connected to reciprocating response to reciprocation of said first shaft; and
   a high vacuum source controlled by said foot pedal and communicating with said second channel to provide a controlled source of increased vacuum to said hand piece, said high vacuum comprising:
   a syringe; and
   a piston activated by said foot pedal to create a vacuum in said syringe.

* * * * *